(12) United States Patent
Boyle

(10) Patent No.: US 6,306,106 B1
(45) Date of Patent: Oct. 23, 2001

(54) DIAGNOSTIC SHEATH FOR REDUCED EMBOLIC RISK

(75) Inventor: William J. Boyle, Santa Clara, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/596,873

(22) Filed: Jun. 19, 2000

(51) Int. Cl.[7] ........................................ A61B 5/00
(52) U.S. Cl. ............................. 600/585; 600/434
(58) Field of Search .................................. 600/434, 435, 600/585; 604/27, 93, 164, 181

(56) References Cited

U.S. PATENT DOCUMENTS

| | | |
|---|---|---|
| 4,564,014 | 1/1986 | Fogarty et al. . |
| 4,927,418 | 5/1990 | Dake et al. . |
| 4,968,306 | 11/1990 | Huss et al. . |
| 4,968,307 | 11/1990 | Dake et al. . |
| 5,021,044 | 6/1991 | Sharkawy . |
| 5,037,403 | 8/1991 | Garcia . |
| 5,046,503 | 9/1991 | Schneiderman . |
| 5,089,005 | 2/1992 | Harada . |
| 5,137,513 | 8/1992 | McInnes et al. . |
| 5,195,971 | 3/1993 | Sirhan . |
| 5,279,562 | 1/1994 | Sirhan et al. . |
| 5,334,154 | 8/1994 | Samson et al. . |
| 5,516,336 | 5/1996 | McInnes et al. . |
| 5,542,925 | 8/1996 | Orth . |
| 5,573,508 | 11/1996 | Thornton . |
| 5,573,509 | 11/1996 | Thornton . |
| 5,611,775 | 3/1997 | Machold et al. . |
| 5,766,203 | 6/1998 | Imran et al. . |
| 5,776,140 | 7/1998 | Cottone . |
| 5,779,673 | 7/1998 | Roth et al. . |
| 5,830,181 | 11/1998 | Thornton . |
| 5,968,068 | 10/1999 | Dehdashtian et al. . |

FOREIGN PATENT DOCUMENTS

| | | |
|---|---|---|
| 0 947 211 A2 | 6/1999 | (EP) . |
| WO 96/39997 | 12/1996 | (WO) . |
| WO 98/10713 | 3/1998 | (WO) . |

*Primary Examiner*—Max Hindenburg
(74) *Attorney, Agent, or Firm*—Fulwider Patton Lee & Utecht, LLP

(57) ABSTRACT

This invention is directed to a diagnostic sheath device which is adapted to facilitate atraumatic navigation of intravascular catheters along vascular pathways. The sheath consists of an elongated flexible shaft, having a proximal end and a distal end. The distal end of the shaft is hemispherically-shaped or elongated. A guide wire lumen extends through the shaft, from the proximal end to the distal end, for receiving a guide wire. At least one dye-injection lumen extends through the elongated shaft from the proximal end and joins the guide wire lumen at a point near the distal end of the shaft to provide fluid communication between the injection lumen and the guide wire lumen. The shaft is slidably inserted through the hollow interior of a guide catheter so that the hemispherically-shaped or elongated distal end of the shaft extends beyond the distal end of the guide catheter. Thus, the hemispherically-shaped or elongated distal end cooperates with the guide catheter body to provide a smooth rounded catheter tip which, when advanced along the patient's vasculature, reduces the risk of causing trauma to the blood vessel, freeing plaque from the vessel wall, or creating embolisms in the bloodstream.

10 Claims, 3 Drawing Sheets

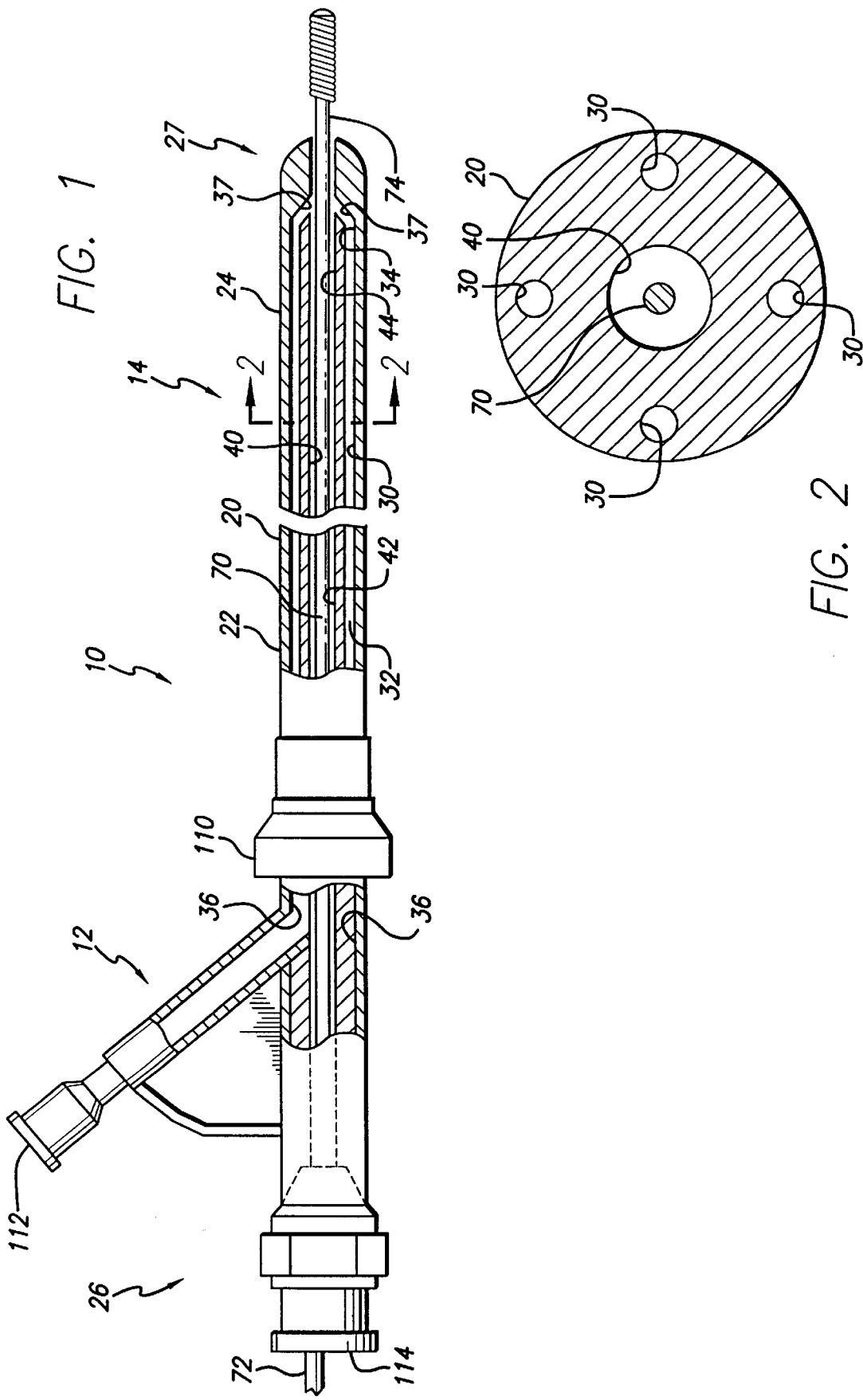

DIAGNOSTIC SHEATH FOR REDUCED EMBOLIC RISK

BACKGROUND OF THE INVENTION

The present invention generally relates to medical devices used in diagnostic testing, which aid the advancement of intravascular catheters through blood vessels for performing interventional vascular diagnosis and treatment procedures. In particular, the present invention pertains to the use of a diagnostic sheath apparatus for facilitating atraumatic navigation of guide catheters along vascular pathways, thereby reducing the risk of causing trauma to the blood vessel, freeing plaque from the vessel wall, or creating emboli in the bloodstream. Additionally, the diagnostic sheath apparatus is capable of injecting contrast dye into the patient's vasculature to assist in the visualization of vascular pathways.

In recent years, a variety of noninvasive intravascular procedures have been developed for the diagnosis and treatment of atherosclerosis, featuring the localized restriction of blood flow through an artery due to the accumulation of atherosclerotic plaque along the artery wall. Most of these noninvasive procedures utilize intravascular catheters to aid the transport of medical devices through the patient's vasculature to reach the arterial blockage since the medical device is typically inserted into the body at a location that is a significant distance away from the treatment site. Once the catheter has been advanced into the desired position, the internal lumen of the catheter is utilized as a guiding sleeve through which various medical devices may be conveniently advanced to the diseased location of the patient's vessel for performing diagnostic or treatment procedures.

As an example, in the treatment of arteriosclerosis, procedures such as percutaneous transluminal coronary angioplasty (PTCA) may be used. In such case, a guide catheter is utilized to provide a conduit through which a dilatation balloon catheter device is conveniently advanced to reach the region of arterial stenosis. In typical coronary angioplasty procedures, the distal end of the guide catheter is introduced percutaneously into the patient's vasculature by way of the femoral artery. A guide catheter is advanced through the descending arteries and past the aortic arch, until the distal tip is properly located near the ostium of the coronary or peripheral artery. The proximal end of the guide catheter is then manipulated so that the distal end of the catheter is aligned with the lumen of a selected artery branching off from the aorta. Once the guide catheter is properly positioned, a guide wire and treatment device are advanced to the distal end of the guide catheter and then the guide wire is advanced into the obstructed artery until the distal tip of the wire extends beyond the stenotic region in the vessel. Thereafter, the treatment device, such as a dilatation balloon angioplasty catheter, a laser catheter, stent delivery system, or an atherectomy catheter is advanced over the guide wire until the distal end of the treatment device is positioned across the stenotic region in the coronary artery. The treatment device is then activated to reduce or remove the stenosis thereby reestablishing unimpeded blood flow through the artery.

Intravascular guide catheters are well known in the medical profession and generally consist of a somewhat flexible cylindrical catheter body having a proximal end and a distal end. In general, guide catheters are configured with an inner lumen extending through the catheter body from the proximal end to the distal end. The inner lumen provides a conduit though which various medical devices are advanced during noninvasive medical procedures. It will be appreciated that the inner diameter of the inner lumen must be sufficiently large as to receive and pass therethrough various treatment devices, such as dilatation catheters, atherectomy catheters, stent delivery systems, and the like. At the same time the outer diameter of the catheter body must be minimized to facilitate advancement of the catheter through vascular passageways. Therefore, the guide catheter body is generally constructed with a thin catheter wall which allows the inner diameter of the inner lumen to be maximized and at the same time provides a catheter body having a minimized outer diameter.

During intravascular treatment procedures, guide catheters must be able to traverse vascular pathways in an atraumatic manner to prevent injury to the patient. Atraumatic navigation along a blood vessel is often frustrated by the generally thin walled cylindrical construction of guide catheters. The hollow cylindrical construction of the catheter body includes an inner lumen having a relatively large inner diameter exposed at the distal end of the catheter. As the catheter is advanced along the vessel, the inner lumen of the catheter slides over the guide wire. As the guide catheter is advanced over the guide wire, the distal edge of the catheter is exposed and is likely to encounter vessel structure and/or plaque deposits along the way. When an obstacle is encountered the distal edges of the catheter embeds in the tissue and tissue matter is allowed to enter the hollow interior of the catheter. As deployment is continued, the distal edges of the catheter either embed into the tissue or flex and deflect away from the obstacle. Either way, the encounter between vessel tissue and the catheter increases the likelihood that tissue is dislodged into the blood stream, thus increasing the risk of embolism.

To reduce the likelihood of trauma to the soft lining of the blood vessels through which the catheter is routed, prior art catheters are configured with a deformable tip which is bonded to the distal end of the guide catheter. The deformable tip is generally a hollow cylinder formed from a polyurethane hybrid material having a lower durometer than the plastic comprising the remainder of the catheter. The soft tip may be adhesively bonded to the catheter and otherwise configured as a means to reduce the likelihood of trauma to the soft lining of the blood vessels.

A problem encountered with prior art catheter designs of this type is the limited bondable surface area between the thin wall catheter body and the deformable tip. Due to this limitation, the deformable tip may not be able to form a secure bond with the catheter body, leading to possibilities of separation of the deformable tip from the catheter body during use. Another problem with deformable tip catheters is the tendency of the soft deformable tip to buckle as the catheter encounters an obstruction during the advancement of the catheter along vessel which may lead to difficulties in controlling the navigation of the catheter device along the patient's vasculature.

In addition to assisting in the delivery of a guide catheter, during vascular therapy such as an angioplasty procedure or the stenting of a diseased area, it is highly desirable to be able to inject a contrast medium such as a radiopaque dye into the vessel upstream of the diseased site in order to check the flow past the site. This enables the physician to precisely locate the stenosis and assist in properly positioning the treatment device prior to treatment. After treatment, the injection of dye allows a determination to be made as to whether the procedure was successful or whether further treatment of the site, manipulation of the stent, or some other procedure is necessary.

Therefore, it is desirable for a diagnostic sheath catheter to provide a means for injecting radiopaque contrast dye, or the like, into the cardiovascular system to assist the visualization of occluded vascular pathways. In typical interventional angiography procedures, a catheter is advanced along the patient's vasculature while at the same time injecting contrast dye into the blood stream. The dye is then observed using flouroscopy techniques to visualize the patient's vascular pathways. During interventional procedures, the catheter is advanced along descending arteries until the distal tip of the catheter is properly located near the ostium of the artery. At the diseased location, additional contrast dye is then injected into the blood vessels to visualize occluded regions of the artery. Once the vascular obstruction has been identified, various treatment procedures may be performed to reduce or remove the arterial blockage, thereby reestablishing unimpeded blood flow through the artery.

Other intravascular devices have been described which purport to aid the advancement of catheters and allow for the injection of fluids into the bloodstream. One prior art method describes a telescoping guide catheter system having two single lumen guide catheters, wherein a first guide catheter slidably receives a second guide catheter. A working catheter may be passed through the inner lumen of the second guide catheter and fluids may be perfused between the inner lumen of the first guide catheter and the exterior of the second guide catheter. However, even distribution of injection dye fluid may be difficult to achieve.

Accordingly, what is needed and heretofore unavailable is a device which facilitates atraumatic navigation of intravascular guide catheters along the tortuous passageways of a patient's vasculature which minimizes or eliminates the problems associated with tip separation and is sufficiently stable in order to increase control during navigation. Additionally, the device must be adapted to receive a guide wire and be capable of consistently injecting contrast fluid into the bloodstream to assist in the visualization of vascular pathways. The present invention satisfies these and other needs.

SUMMARY OF THE INVENTION

The present invention is directed to a diagnostic sheath device, which may be utilized in a variety of ways in interventional vascular procedures. First it may be utilized as a delivery/navigation tool to reduce the risk of embolic events during advancement of a guide catheter during interventional vascular procedures and second, it may be utilized as a dye-injection tool to aid in the visualization of vascular pathways and occluded regions of the artery.

For use as a delivery/navigation tool, the device is designed to be used in combination with a standard guide catheter to provide atraumatic advancement of the guide catheter through the human vasculature. In this case, the diagnostic sheath device may be utilized as an ancillary tool which facilitates the advancement and manipulation of the guide catheter. The diagnostic sheath device consists of an elongated flexible shaft having a proximal end and a distal end. The distal end of the shaft has a smooth dome-shaped configuration. A guide wire lumen extends through the entire axial length of the elongated shaft and extends to the distal end. At the proximal end of the device the guide wire lumen is coupled to an adapter having a guide wire lumen port in communication with the guide wire lumen for reception of a typical guide wire. The hemispherically-shaped or elongated nose cone assists the delivery of a guide catheter by providing a continuously dome-shaped or elongated distal end which reduces the risk of vascular tissue being dislodged and subsequently embolize during delivery of the guide catheter into the patient's vasculature.

In use, during advancement through the patient's vasculature, when the catheter device encounters the vessel wall, a region of atherosclerotic plaque along the vessel wall, or other obstructions, the smooth curved shape of the distal end of the diagnostic sheath device contacts the obstruction and deflects the catheter device away from the obstacle without causiny injury to the vessel or dislodging material into the bloodstream. Thereby, the catheter device may continue to advance along the vessel without causing any injury.

Another aspect of the present invention is that it may be use as a dye-injection tool. The diagnostic sheath includes a plurality of dye-injection lumens that axially extend through the elongated shaft of the diagnostic sheath from the proximal end to a position near the distal tip of the elongated shaft where the dye-injection lumens then project radially inwardly at a preselected angle to join the guide wire lumen, thereby allowing fluid communication between the respective dye-injection lumens and the guide wire lumen for injection of radiopaque dye through the diagnostic sheath device. At the proximal end of the device, the dye-injection lumens are in fluid communication with a single dye-injection port located at the device proximal end. The dye-injection port is adapted to receive a dye reserve and allows dye to be injected into the plurality of dye-injection lumens for delivery into the patient's vasculature.

In an alternative embodiment, the guide wire lumen in the diagnositc sheath extends through only a portion of the sheath. An exit port is positioned on the sheath outer wall surface at a point that is proximal to the catheter distal end, but closer to the distal end than the proximal end of the sheath. The sheath can then be rapidly exchanged with other devices while the guide wire remains in place in the vasculature.

Other features and advantages of the present invention will become apparent from the following detailed description, taken in conjunction with the accompanying drawings, which illustrate, by way of example, the principles of the invention.

BRIEF DESCRIPTION OF THE DRAWINGS

The following drawings are referenced in the text of the detailed description of the invention. Several figures are presented in which like numerals in different figures refer to identical parts.

FIG. 1 is a plan view, partially in section, of one embodiment of the present invention.

FIG. 2 is a transverse cross-sectional view of the embodiment shown in FIG. 1 taken along lines 2—2, depicting the location of a guide wire lumen and radiopaque dye-injection lumens.

DETAILED DESCRIPTION OF THE PREFERRED EMBODIMENTS

Figure 3:
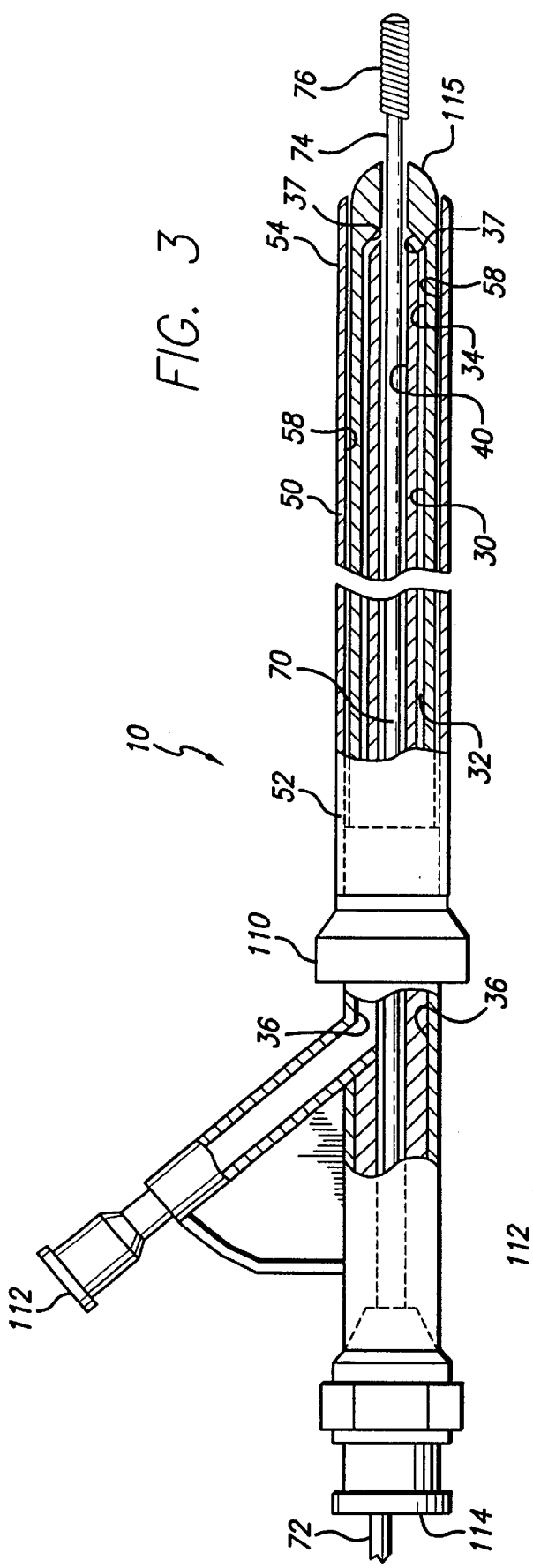
FIG. 3 is a longitudinal plan view, partially in section, of the diagnostic sheath device, wherein the diagnostic sheath device is disposed within a guide catheter for assisting in the atraumatic delivery of the guide catheter through the patient's vasculature.

The present invention is directed to a diagnostic tool used in intravascular procedures for assisting in both atraumatic delivery of a guide catheter and visualization of vascular pathways. More particularly, the present invention is directed to a diagnostic sheath device which provides for atraumatic navigation of guide catheters along vascular pathways by providing a hemispherically-shaped or elongated distal end which allows for smooth advancement of a guide catheter. Additionally, the present invention provides multiple injection lumens for the delivery of contrast dye to the vessel which facilitates the visualization of vascular pathways.

Referring to FIGS. 1 and 2, a diagnostic sheath device 10 includes a proximal end 12 and a distal end 14, and consists of an elongated flexible shaft 20 having a proximal section 22 and a distal section 24. The shaft further includes a proximal end 26 and a distal end 27. The shaft distal end is hemispherically-shaped or elongated so that during use, when the distal end comes in contact with vascular tissue, there will be a reduction in tissue dislodge, thereby minimizing the likelihood of emboli. The diagnostic sheath device includes a guide wire lumen 40 having a proximal end 42 and a distal end 44. The guide wire lumen extends throughout the center of the shaft, from the shaft proximal end to the shaft distal end and is configured for receiving a guide wire 70. Additionally, the device further includes a plurality of dye-injection lumens 30, which have proximal ends 36 and distal ends 37. The dye-injection lumens extend through the shaft in parallel with the guide wire lumen from the shaft proximal end to a point near the shaft distal end. The plurality of injection lumens are positioned concentrically about guide wire lumen and evenly spaced apart across the cross section of catheter shaft (FIG. 2). At a point in the shaft distal section, just proximal to the shaft distal end, the injection lumens project radially inward and communicate with the guide wire lumen distal section. This configuration provides a convergence between the plurality of injection lumens and guide wire lumen at the diagnostic sheath distal section.

The diagnostic sheath proximal section 12 includes adapter 110. The adapter includes a dye-injection port 112 and a guide wire lumen port 114. The dye-injection port is connected to all of the injection lumens 30 and, allows for the introduction of radioplaque contrast dye into the plurality of dye-injection lumens. The guide wire port is connected to the guide wire lumen 40 and is configured for slidingly receiving a guide wire 70 into the guide wire lumen.

Referring to FIG. 3, the diagnostic sheath device 10 is configured to inserted into a guide catheter 50. The outer diameter of the diagnostic sheath's flexible shaft 20 is sized to allow it to be inserted into the guide catheter. The guide catheter has a proximal end 52 and distal end 54 and has a through lumen 58 for receiving the diagnostic sheath. Once placed over the diagnostic sheath, the guide catheter proximal section is secured to adapter 110 of the diagnostic sheath proximal section 12. The adapter is capable of securing the guide catheter proximal end thereby preventing relative motion between the guide catheter and the concentrically disposed diagnostic sheath device. A hemostasis valve connected to the proximal end of the guide catheter may also secure the guide to the diagnostic sheath.

It will be appreciated that the of the present invention can be sized to be used with catheters having various internal diameters. The chosen length of the diagnostic sheath device 10 is slightly longer that the length of the guide catheter 50 so that when the diagnostic sheath device is disposed within the guide catheter, the guide catheter distal end 54 corresponds to sheath shaft distal end 27 such that the distal extremity of the sheath shaft, which is hemispherically-shaped or elongated or dome-shaped, slightly protrudes distally of guide catheter distal end. The protrusion of the curved shaped shaft distal end aids the delivery of the guide catheter through the patient's vasculature by deflecting away obstacles and obstructions along the vessel without causing injury to the vessel or dislodging material into the bloodstream. Once the guide catheter has been advanced to the desired site, the diagnostic sheath may be removed from the guide catheter and replaced with balloon angioplasty catheters or the like for treating the diseased site.

Figure 4:
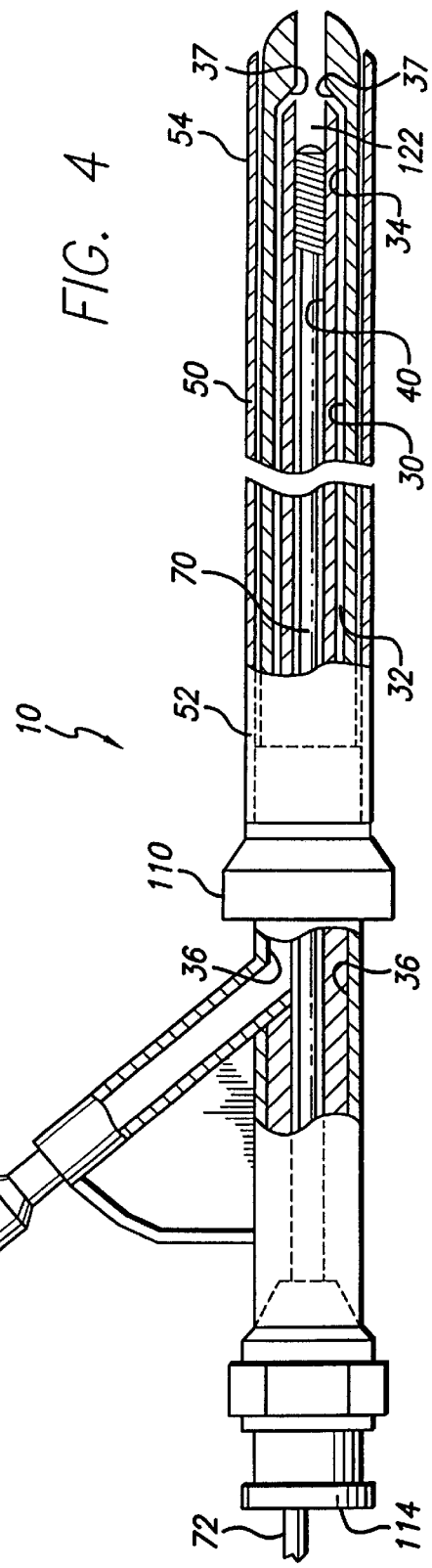
FIG. 4 is a longitudinal plan view of the diagnostic sheath wherein a guide wire is in a retracted positioned allowing for the introduction of radioplaque dye flow from the dye-injection lumens into the guide wire lumen for release into the patient's vessel.

Referring to FIG. 4, the diagnostic sheath device 10 may be utilized as a dye-injection tool to assist in visualizing vascular pathways. In this case, radioplaque contrast dye is delivered to the patient's vessel by injecting dye into the injection lumens 30 where the dye is delivered via the diagnostic sheath device to the vessel. The injection lumens, in the device distal section 14 protrude radially inward to connect to the guide wire lumen 40. During use as a dye-injection tool, a guide wire 70 is positioned at a location 122 just proximal to the area of convergence between the injection lumens and the guide wire lumen. This position allows the guide wire to remain within the guide wire lumen while not blocking or obstructing the flow of dye from the injection lumens into the guide wire lumen. Additionally, the positioning of the guide wire reduces the likelihood of back flow of contrast dye into the proximal sections of the diagnostic sheath device, instead it serves to vector contrast dye in a distal direction out of the device into the patient's vessel.

Figure 5:
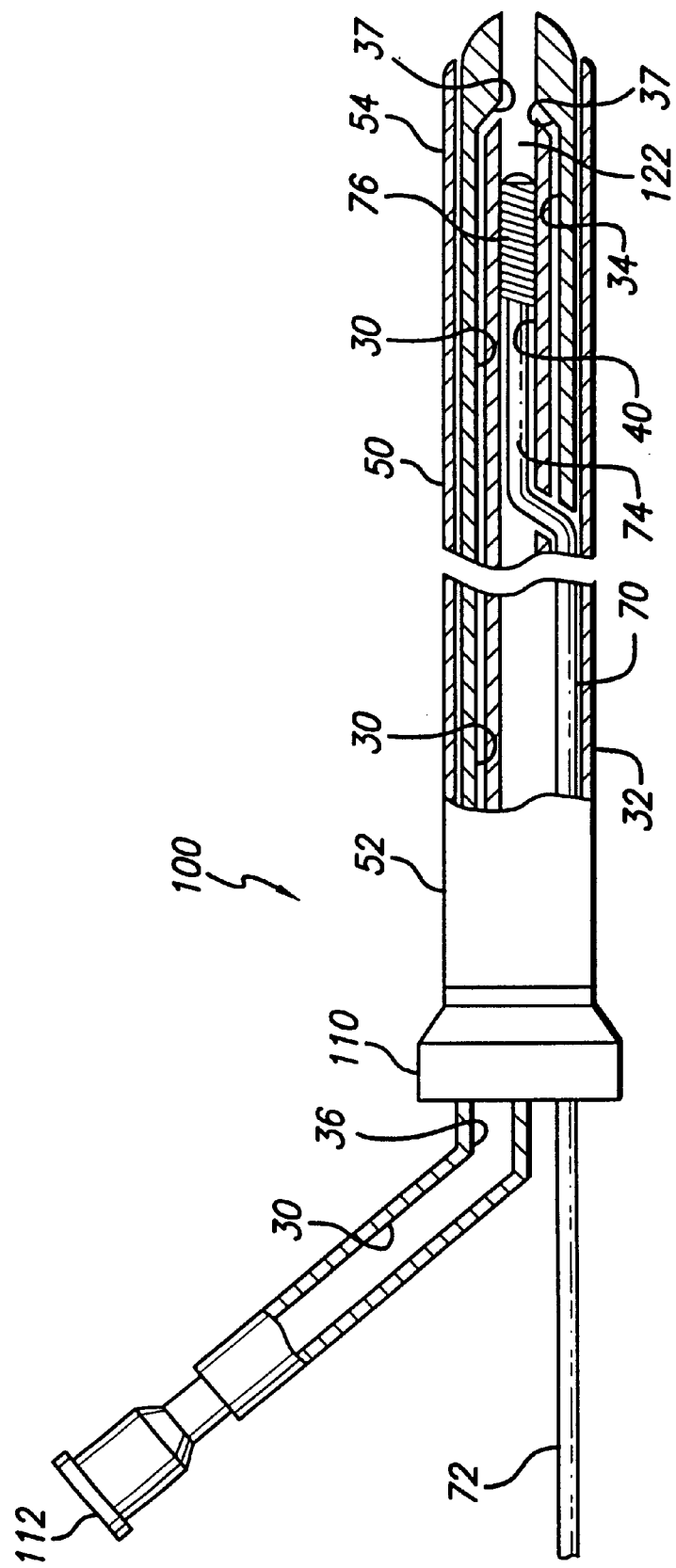
FIG. 5 is a longitudinal plan view, partially in section, depicting an alternative embodiment in which the guide wire lumen is of the rapid-exchange type, extending through only a portion of the diagnostic sheath.

In an alternative embodiment, as shown in FIG. 5, the diagnostic sheath 10 has a guide wire lumen 60 that extends through only a portion of the diagnostic sheath. In this embodiment, the diagnostic sheath is of the rapid-exchange type, which permits the physician to rapidly remove the diagnostic sheath from the guiding catheter and exchange it for an angioplasty catheter or other device for further medical procedures, with the guide wire remaining in place in the patient's vasculature. The guide wire lumen extends from a distal port 61 to a proximal port 63, with the proximal port exiting the catheter on the outer surface 64 of the sheath. The proximal port typically is positioned closer to the distal end 65 of the sheath than the proximal end 66. It is contemplated that a slit (not shown) extends from the proximal port 63 in a distal direction toward the distal end of the diagnostic sheath so that the guide wire can be pulled through the slit (in a known manner) when the diagnostic sheath is removed from the patient and the guide wire held in place for subsequent procedures.

The diagnostic sheath 10 can be formed from conventional biocompatible materials such as melt processable thennoplastic polymers, e.g., polyethylene, polyethylene terephthalate, polyester-polyamide such as HYTREL.RTM, and an ionomer such as SURLYN.RTM, which are available from the E. I. DuPont, deNemours & Company. The diagnostic sheath device 10 can be formed in a laminate construction, e.g., where one layer of the laminate is a relatively high strength to provide relative stiffness, e.g., polyethylene terephthalate or a high density polyethylene, and the other layer is a relatively low strength but more flexible to provide good flexibility for tracking, e.g., a polyester-polyamide such as Hytrel.RTM, a low density polyethylene or a suitable polyurethane. Braided or wound supporting strand may be incorporated into the wall of the diagnostic sheath device shaft 20 to provide, in whole or in part, stiffness while maintaining flexibility. Fabrication of the diagnostic sheath device may be conveniently done by conventional injection molding or extrusion techniques.

While a particular form of the invention has been illustrated and described, it also will be apparent to those skilled in the art that various modifications can be made without departing from the spirit and scope of the invention. Accordingly, it is not intended that the invention be limited except by the appended claims.

What is claimed:

1. A diagnostic sheath assembly for facilitating atraumatic navigation of guide catheters along vascular pathways, comprising:
    an elongated catheter body having a proximal end and a distal end;
    an elongated shaft disposed in the elongated catheter body and extending from the proximal end to the distal end of the catheter body, the elongated shaft having a proximal end and a distal end;
    a guide wire lumen extending through the elongated shaft from the proximal end to the distal end for receiving a guide wire;
    at least one dye-injection lumen extending through the elongated shaft from the proximal end and joining the guide wire lumen at a point near the distal end of the shaft to provide fluid communication between the at least one dye-injection lumen and the guide wire lumen.

2. The diagnostic sheath assembly of claim 1, wherein the shaft distal end is dome-shaped or elongated and is positioned relative to the catheter body such that the dome-shaped or elongated distal end extends beyond the distal end of the catheter body.

3. The diagnostic sheath assembly of claim 2, wherein the dome-shaped or elongated distal end has a smoothly curved conical shape.

4. The diagnostic sheath assembly of claim 1, wherein the elongated catheter body is a guide catheter.

5. The diagnostic sheath assembly of claim 1, further comprising a plurality of dye-injection lumens extending through the elongated shaft from the proximal end and joining the guide wire lumen at a point near the distal end of the shaft to provide fluid communication between the dye-injection lumen and the guide wire lumen.

6. A diagnostic sheath for facilitating atraumatic navigation of guide catheters along vascular pathways, comprising:
    an elongated shaft configured for insertion into a guide catheter, the elongated shaft having a proximal end and a distal end;
    a guide wire lumen extending through the elongated shaft from a proximal end to a distal end for receiving a guide wire;
    at least one dye-injection lumen extending through the elongated shaft from the proximal end and joining the guide wire lumen at a point near the distal end of the shaft to provide fluid communication between the at least one dye-injection lumen and the guide wire lumen; and
    the shaft distal end having a dome-shaped or elongated configuration and positioned relative to the guide catheter such that the dome-shaped or elongated distal end extends slightly beyond the distal end of the catheter body.

7. A diagnostic sheath of claim 6, wherein the dome-shaped or elongated distal end has a smoothly curved conical shape.

8. A diagnostic sheath assembly for facilitating atraumatic navigation of guide catheters along vascular pathways, comprising:
    an elongated catheter body having a proximal end and a distal end;
    an elongated shaft disposed in the elongated catheter body and extending from the proximal end to the distal end of the catheter body, the elongated shaft having a proximal end and a distal end;
    a guide wire lumen extending through at least a portion of the elongated shaft from a distal port at the distal end of the elongated shaft to a proximal port positioned proximally of the distal end port, the guide wire lumen being configured for receiving a guide wire; and
    at least one dye-injection lumen extending through the elongated shaft from the proximal end and joining the guide wire lumen at a point near the distal end of the shaft to provide fluid communication between the at least one dye-injection lumen and the guide wire lumen.

9. The diagnostic sheath of claim 8, wherein the shaft distal end is dome-shaped or elongated and is positioned relative to the catheter body such that the dome-shaped or elongated distal end extends beyond the distal end of the catheter body.

10. The diagnostic sheath of claim 9, wherein the dome-shaped distal end has a smoothly curved conical shape.

* * * * *

UNITED STATES PATENT AND TRADEMARK OFFICE
CERTIFICATE OF CORRECTION

PATENT NO. : 6,306,106 B1  Page 1 of 1
DATED : October 23, 2001
INVENTOR(S) : William J. Boyle It is certified that error appears in the above-identified patent and that said Letters Patent is hereby corrected as shown below:

<u>Title page, Item [54], and Column 1, lines 2-3,</u>
Title, delete "FOR REDUCED EMBOLIC RISK".

Signed and Sealed this

Twenty-sixth Day of March, 2002

*Attest:*

*Attesting Officer*

JAMES E. ROGAN
*Director of the United States Patent and Trademark Office*